United States Patent [19]
Norwood

[11] Patent Number: 5,247,931
[45] Date of Patent: Sep. 28, 1993

[54] DIAGNOSTIC SENSOR CLASP UTILIZING A SLOT, PIVOT AND SPRING HINGE MECHANISM

[75] Inventor: Mark D. Norwood, Baltimore, Md.

[73] Assignee: Mine Safety Appliances Company, Pittsburgh, Pa.

[21] Appl. No.: 760,507

[22] Filed: Sep. 16, 1991

[51] Int. Cl.⁵ .............................................. A61B 5/00
[52] U.S. Cl. .................................. 128/633; 128/665; 128/666; 128/672; 356/41; 24/490
[58] Field of Search ............... 128/633, 665, 666, 672, 128/689; 356/41; 24/490

[56] References Cited
U.S. PATENT DOCUMENTS

| | | | |
|---|---|---|---|
| 2,118,475 | 5/1938 | Pallas | 24/490 |
| 3,373,465 | 3/1968 | Johnson et al. | 24/490 |
| 4,334,544 | 6/1982 | Hill et al. | 128/666 |
| 4,685,464 | 8/1987 | Goldberger et al. | 128/666 |
| 4,913,150 | 4/1990 | Cheung et al. | 128/665 |

FOREIGN PATENT DOCUMENTS 0354455 6/1922 Fed. Rep. of Germany ........ 24/490

Primary Examiner—David Isabella
Assistant Examiner—Paul Prebilic

[57] ABSTRACT

A hinge clamp mechanism and sensor for performing pulse oximetry tests, as well as for performing other diagnostic procedures that can be conducted on a human body part, such as a finger. More particularly, the hinge clamp mechanism utilizes one or more slots, pins and springs to enclose the body part being tested. The hinge clamp relies on a movable pivot point connecting upper and lower portions of the device and the biasing force of one or more cantilevered leaf springs to enable the upper and lower body portions of the device to conform to the upper and lower surfaces of the body part, and to evenly distribute the gripping pressure of the device over the upper and lower surfaces of the body part.

23 Claims, 3 Drawing Sheets

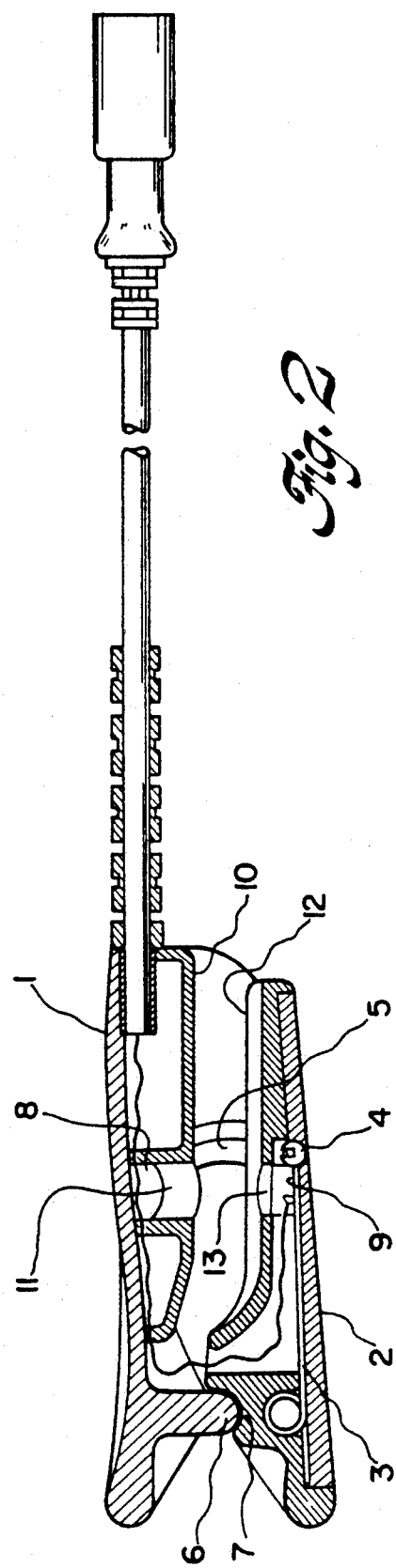
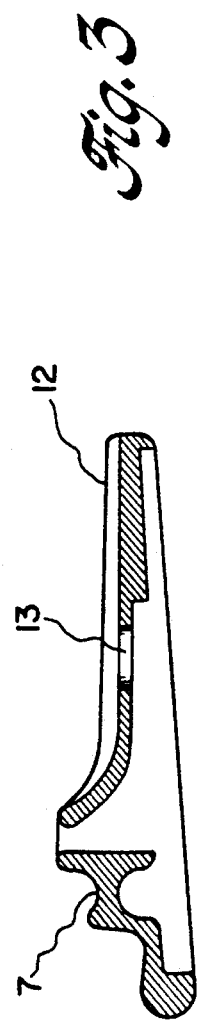
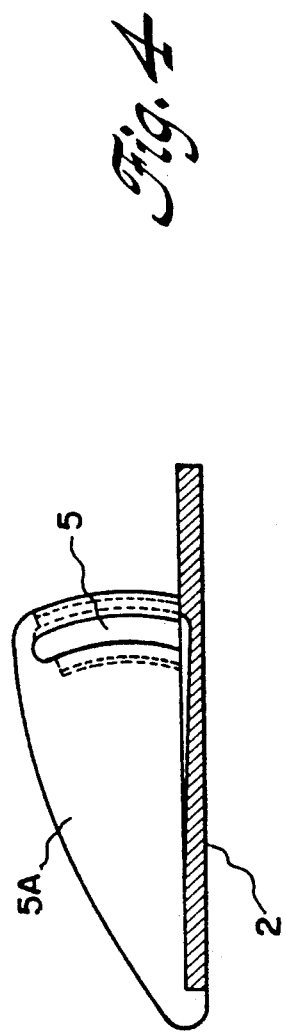
Fig. 2
Fig. 3
Fig. 4

DIAGNOSTIC SENSOR CLASP UTILIZING A SLOT, PIVOT AND SPRING HINGE MECHANISM

FIELD OF THE INVENTION

The present invention relates to a hinge mechanism and more particularly to the hinge clamp mechanism used in a finger sensor designed for oximetry measurements and similar diagnostic procedures.

BACKGROUND OF THE INVENTION

Pulse oximetry is a non-invasive medical technique useful for measuring certain vascular conditions, wherein light is passed through a portion of a patient's body which contains arterial blood flow. An optical sensor is used to detect the light which is passed through the body and variations in the detected light at various wave lengths are then used to determine arterial oxygen saturation and/or pulse rates. Oxygen saturation may be calculated using some form of the classical absorption equation known as Beer's law.

Accurate measurements of these and other physiological functions are predicated upon optical sensing in the presence of arterial blood flow. An ear lobe or a finger may conveniently serve for this purpose, since each is an easily accessible body part through which light will readily pass. U.S. Pat. Nos. 4,825,872 and 4,825,879 describe finger sensors which wrap around the finger to thereby permit oximetry measurements to be made. The disadvantage with these devices is that they are either cumbersome to attach to the finger or do not provide solid contact between the finger and the sensor.

U.S. Pat. No. 4,685,464 shows another pulse oximetry sensor using a clothes pin type device. The advantage with this device is that it is very easy to attach to the patient. The disadvantage with this device is that the traditional clothes pin spring mechanism, does not allow the upper and lower halves of the sensor to lie parallel to the upper and lower surfaces of the finger. Rather than clamping the surfaces of the finger with consistent pressure and even physical contact, such devices do not conform to the actual dimensions of the upper and lower surfaces of the finger. The interior angle of the inner surfaces of such clamps are limited by their simple fixed pivot point design to whatever angle results from the thickness of the finger being clamped, rather than the actual angle of the finger's surfaces. As a result, such fixed pivot point, spring clamp mechanisms unevenly concentrate the pressure created by the spring on the points of the finger that happen to contact the inside surfaces of the clamp's upper and lower halves, rather than evenly distributing physical contact and balancing the gripping pressure over the desired contact surfaces of the finger, thereby resulting in localized constriction which decreases the flow of blood and otherwise creates an unnatural or artificial condition.

Clamps for fingers and other body parts are called upon to make critical, highly sensitive and easily disrupted optical and other medical sensory measurements and tests. Proper measurement of physiological functions such as arterial blood flow depends on the ability of a clamp to firmly yet gently grasp the surface of the region being tested so as to make a "quality" contact, thereby permitting accurate optical or electrical/resistive measurements as well as other advanced and conventional sensing techniques. The only way a clothes pin type clamp can obtain the proper physical contact with the surfaces of the finger is if the thickness and angle of the finger surfaces just happen to match the angle of the fixed pivot point jaw and the resultant distances between the clamp's inner surfaces. Otherwise, the only way to obtain sufficient physical contact with the region being tested using a clamp with a fixed pivot point is to increase the pressure on the body part, thereby causing that body part to conform to the predetermined dimensions of the clamp. In short, a clothes pin type clamp not only can result in an inaccurate sensory measurement due to inconsistent surface contact and pressure, but can actually induce an error through the constrictive conditions it creates.

It would be desirable therefore if a clamping device for a sensor could be developed which utilized a hinge mechanism which did not have the disadvantages of the fixed pivot point clamp, and which permitted the upper and lower halves of the sensor clamp to adjust to the dimensions of the body part being sensed so as to lie parallel to the upper and lower surfaces of that body part. Such a device should be capable of gently grasping the surface(s) being sensed with even contact and pressure, despite the infinite combinations of the angle or slope between the surfaces being contacted and the distances between those surfaces (e.g. the thickness of the ear lobe or finger). It is also desirable that the device should conform to the surfaces being contacted, rather than those surface being forced to conform to the dimensions and properties of the clamping device.

Finally, for those instances when increasing the physical pressure on the body part being evaluated is desired or even required as part of the test procedure, the clamping device should have inner surfaces that will adjustably conform to the surface being tested while applying increased yet evenly distributed pressure, without forcing or distorting the body part being tested to conform to the inner surfaces of that clamping device.

SUMMARY OF THE INVENTION

Generally, the present invention relates to a hinge clamp mechanism and more particularly to one which is used in a pulse oximetry or similar sensor for medical diagnostic procedures. The movable pivot point design of the present invention permits the gripping surfaces of the hinge clamp to lie in contact with and parallel to the upper and lower surfaces of the human body part being clamped such as a finger or an ear lobe. The hinge clamp comprises a first portion and a second portion joined together by means of a guide pin movable in a coinciding guide pin slot. Preferably, the first portion has two guide pins, each one being inserted into a guide pin slot located on one side of the second portion. Additionally, the first and second portions each have a pivot pin attached thereto, which can be in pivoting engagement with each other or which can be separated from one another. The guide pins and coinciding guide pin slots are displaced from the pivot pins and provide a means for keeping the first and second portions connected when the hinge clamp is open. One or more springs are attached at one end to the second portion and at the other end to the first portion, preferably at the guide pins such that the spring biases the first portion towards the second portion. The pivot pins may lie between the ends of the spring or be aligned with the spring mounting point.

The movable guide pin of the present invention, regardless of the angle or slope difference and distance between the surfaces of the body part being clamped, permits the inner surfaces of the first and second portions of the hinge clamp to adjust to the dimensions of the body part. In this way, the hinge clamp is capable of firmly yet gently gripping a body part with even pressure from the inner surfaces of the hinge clamp. It does this by first pivoting at the pivot pins to allow a body part to be inserted. Then, the pivot pins separate while the guide pins hold the first and second portions aligned. The guide pins also move in the guide pin slots to accommodate the size of the body part. The guide pins now act as pivot points so that the first and second portions can be positioned parallel to the surfaces of the body part. Despite the various combinations of the angle or slope between the surfaces of the body part being clamped and the distances between those surfaces, the hinge clamp of the present invention adjustably conforms to the surfaces being clamped due to the movable guide pins and the movable pivot point, rather than distorting those surfaces to conform to the dimensions of the clamp hinge itself as in a fixed pivot point hinge.

When increased surface pressure on the body part being evaluated is part of the test being conducted, the present device is capable of applying that increased pressure without sacrificing the even distribution of pressure applied by the hinge clamp, and again without distorting the surface being tested or unevenly applying that increased pressure.

The hinge clamp of the present invention equally distributes pressure along the body part surfaces being held, regardless of the dimensions of those surfaces or the amount of pressure to be applied to those surfaces. When used to conduct oximetry tests, the finger or other body part of a patient is sensed using the movable pivot point action of the present invention coupled with an oximeter probe device. A certain amount of pressure is required to effectively secure a pulse oximetry light emitter and corresponding light sensor apparatus to a patient. Equal distribution of that pressure is critical to obtaining precise oximetry measurements as excessive pressure or pressure that otherwise distorts or constricts the body part can unnaturally alter a patient's blood flow, causing an inaccurate measurement of blood oxygen levels.

Similarly, other advanced as well as conventional sensing techniques that can employ the hinge clamp of the present invention require that the sensing device make proper contact with the body part being tested, without altering or otherwise disrupting the blood flow or other natural conditions of the body part being tested, as such effects can result in inaccurate measurements or readings in these tests as well. The false conditions created by clamps that fail in this regard may go undetected by clinical personnel and diagnostic equipment, resulting in misdiagnosis and possibly leading to incorrect medical treatment. Further, pressure concentrations resulting from improper use of a sensing clamp may also cause discomfort for the patient, and may damage human tissue.

Other details, objects and advantages of the present invention will become apparent as the following description of the presently preferred embodiments of practicing the invention proceeds.

BRIEF DESCRIPTION OF THE DRAWINGS

In the accompanying drawings, the preferred embodiments of the invention are illustrated in which:

FIG. 2 shows a sectional side view of a preferred embodiment of the present invention;

FIG. 3 shows a sectional side view of an inner support member attached to an interior surface of a second portion of the clamp mechanism;

FIG. 4 shows a sectional side view of the second portion of the clamp mechanism with the inner support member removed.

DETAILED DESCRIPTION OF THE INVENTION

Figure 1:
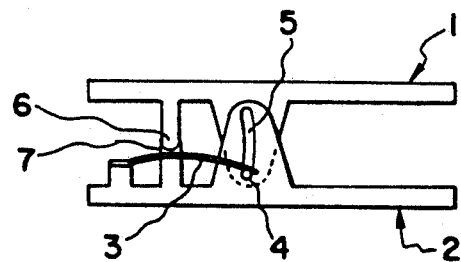
FIG. 1 is a schematic representation of the present invention.

FIG. 1 shows a schematic representation of the present invention wherein a first or "upper" portion 1 and a second or "lower" portion 2 of a clamp mechanism are held together by a spring 3, in this instance, a leaf spring. One end of spring 3 is connected to the lower portion 2 and the other end is connected to guide pin 4 which, in turn, is connected to and forms part of upper portion 1. Guide pin 4 is movably enclosed in guide slot 5 of the lower body portion 2. A pivot pin 6 is carried by upper portion 1 and normally is pivotally supported in a pivot receiving seat 7 formed in lower portion 2. However, as will be described hereinbelow pivot pin 6 and pivot pin receiving seat 7 are also separable and relatively displaceable away from one another.

Figure 1A:
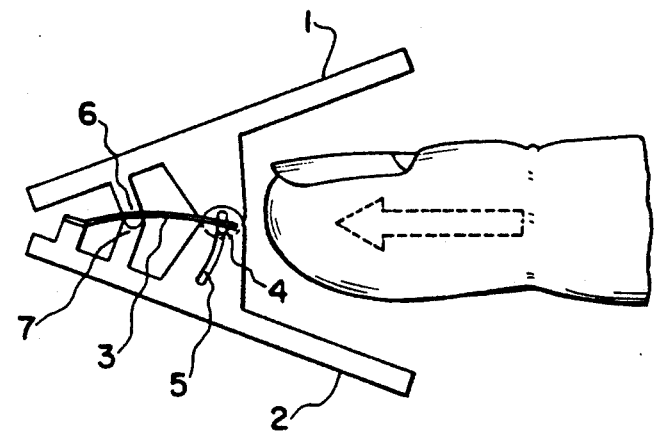
FIG. 1A is a schematic representation of the present invention, wherein the hinge clamp mechanism is in the open position ready to receive a patient's finger.
Figure 1B:
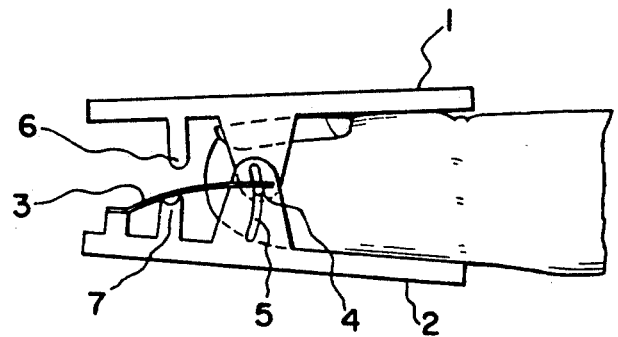
FIG. 1B is a schematic representation of the present invention, wherein the hinge clamp mechanism is in the closed position around a patient's finger.

A set of the aforementioned elements including spring 3, guide pin 4, guide slot 5, pivot pin 6 and pivot pin receiving seat 7 are located along one side of the upper and lower body halves with a similar set of elements being positioned in mirror image on the other side so that a body part, e.g., a finger, can be inserted therebetween such as shown in FIGS. 1A and 1B.

FIG. 1A is a schematic representation of the present invention depicting upper portion 1 and lower portion 2 of the clamp mechanism in an open position ready to receive a patient's finger. To open the hinge clamp, the operator applies pressure at one end of upper portion 1 and lower portion 2 opposite the ends that receive the body part to be gripped by the hinge clamp. This causes the portions 1 and 2 to pivot about pivot pin 6, thereby opening the hinge to receive the body part. As the pressure from the operator is removed, a closing or restoring force is supplied by spring 3 which causes the portions 1 and 2 to pivot closed about pivot pin 6. When the portions 1 and 2 encounter a body part, however, the presence of the body part causes pivot pin 6 and its seat 7 to separate since they are not fixedly attached to one another. This causes the pivot point of the clamp mechanism to shift to guide pin 4. Guide pin 4, however, is movable in guide slot 5 and will continue to move until the upper portion 1 and lower portion 2 are parallel to the upper and lower surfaces of the inserted body part. FIG. 1B shows the hinge clamp in a closed position around, in this case, a patient's finger, and shows the hinge clamp's ability to conform to the surfaces that it is gripping.

A preferred embodiment of the present invention is shown in the cutaway view of FIG. 2, wherein like references indicate similar elements, as is true remaining views. FIG. 2 shows upper portion 1 and lower portion 2, held together by spring 3, in a manner similar to that described hereinabove. (Only the right side of this embodiment is shown in FIG. 2; the right side of the device as shown is a mirror image of the left side of the hinge clamp mechanism, which is not shown.) Spring 3 is in this instance, a coiled wire torsion spring, is attached to movable guide pin 4 at its one end. At its other end, spring 3 is attached to lower portion 2 at a location generally opposite the end of the clamp mechanism where the body part to be tested is inserted into the mechanism. Preferably, movable guide pin 4 protrudes from and is immovably attached to a surface of upper portion 1. Guide pin 4 is movably enclosed in guide slot 5, as is perhaps most clearly seen in FIG. 4, which is formed in an outer flange surface 5A of lower portion 2 and guide slot 5 is preferably open on its lower end and closed on the upper end thereof.

According to this particular embodiment, pivot pin 6 is attached to and protrudes from an inner surface of upper portion 1, and is in general vertical alignment with the point of attachment of spring 3 to lower portion 2. Pivot pin 6 is pivotably supported in an upwardly facing pivot seat 7, which is formed in the upper surface of lower portion 2. As noted above, by compressing the upper and lower portions 1 and 2 of the device opposite the end into which the body part to be tested is inserted, the upper and lower portions 1 and 2 rotate open at the axis of pivot pin 6 to admit the body part. Once the upper and lower portions are released, the restoring force of spring 3 causes the upper and lower portions to close about the inserted body part with the pivot point shifting from pivot pin 6 and seat 7 to guide pin 4 in guide slot 5.

Sensor mechanisms (consisting of in the case of a pulse oximeter, a light source 8 and a light detector 9 as shown in FIG. 2) can be positioned in the upper and lower portions 1 and 2 of the hinge clamp mechanism of the present invention. As an alternative, the sensor mechanism may be remotely mounted. That is, it is also contemplated that the upper and/or lower portions could be provided with suitable fiber optics for transmitting physiological readings taken from the body part to the remote sensor mechanisms. Similarly, electrical/resistive or other advanced as well as conventional sensing techniques can be carried out using the hinge clamp mechanism of the present invention. The required sensors can be placed at the desired locations on the inner surfaces of the upper and/or lower portions 1 and 2, so as to conduct the necessary tests, measurements and/or readings on the body part. Movable guide pin 4 permits balanced pressure to be applied via the biasing, or restoring force supplied by spring 3 so as to permit accurate testing on the body part inserted between upper and lower portions 1 and 2 of the device.

Figure 2A:
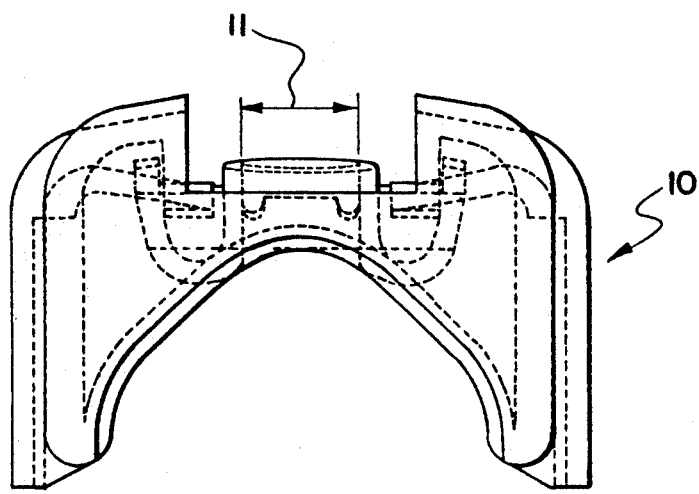
FIG. 2A shows an end view of the contoured inner surface for the upper body half cushion for the embodiment shown in FIG. 2.

FIG. 2 also shows a partial side cutaway view of a cushion 10 attached to the interior surface of upper portion 1 for gripping the body part. An end view of cushion 10 (facing in the direction in which a body part is inserted into the hinge clamp mechanism) is shown in FIG. 2A, wherein the contoured surface for holding a finger in place can be seen. FIGS. 2 and 2A show hole 11, through which, for example, light from light source 8 is able to pass, or through which other desired monitoring, testing, and the like, can be performed. Lower portion 2 has inner support member 12 attached to its interior surface for engaging the lower half of the inserted body part being tested. A partial side cutaway view of inner support member 12 separated from lower portion 2 is shown in FIG. 3, wherein a contoured surface can be seen for supporting a body part, in this case, a finger, in place. The contoured surface can be preformed and/or made from a pliable material such as rubber. A second hole 13 in lower portion inner support member 12 permits light sensor 9 to receive light from light source 8 or permits other tests to be conducted, depending upon the sensor mechanisms carried by the hinge clamp mechanism.

Because of the yieldable construction of the hinge clamp mechanism of the present invention, regardless of the surface configuration and thickness of the body part being grasped (or the distance between the upper and lower surfaces of the body part), the inner surfaces of the portions 1 and 2 adjust to the dimensions of the body part being clamped. As a result, balanced and non-distorting pressure is used to hold the body part while diagnostic procedures are performed.

Figure 5:
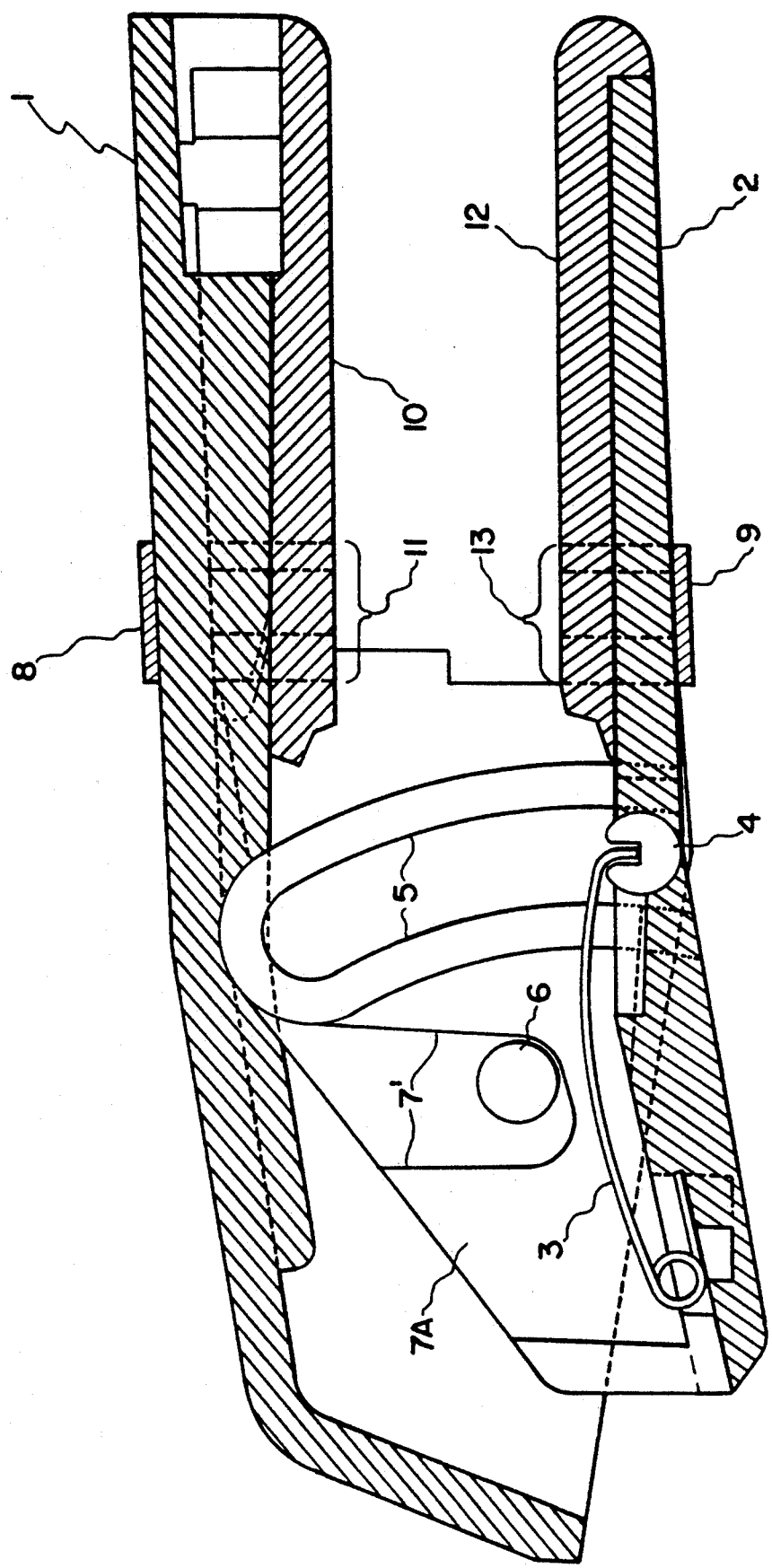
FIG. 5 shows a sectional side view of a further embodiment of the present invention.

Another embodiment of the present invention is shown in the cutaway view of FIG. 5, which corresponds substantially to that shown in the schematic representations of FIGS. 1, 1A and 1B described hereinabove. FIG. 5 shows upper portion 1 and lower portion 2, held together by leaf spring 3. (Only the right side of this embodiment is shown in FIG. 5, it being understood that the left side of the device is a mirror image of the illustrated right side.)

In accordance with this particular embodiment, pivot pin 6 is positioned "behind" (as determined by the direction of body part insertion) and above movable guide pin 4, i.e., to the left and above movable guide pin 4 as shown in FIG. 5. As in the embodiment of the invention shown in FIG. 2, pivot pin 6 is immovably attached to and protrudes from an inner surface of upper portion 1. However, in this embodiment, pivot pin 6 is movably received in a pivot seat in the form of a slot 7', which is formed in a flange surface 7A of lower portion 2. Pivot slot 7' is open on its upper end and closed on its lower end. Again, by compressing the upper and lower portions 1 and 2 of the device opposite the end into which the body part to be tested is inserted, the upper and lower portions 1 and 2 rotate open at the axis of pivot pin 6 to admit the body part. And, as with the previously discussed embodiment, once the body portions are released, spring 3 causes the upper and lower portions of the device to close about the inserted body part with the pivot point shifting from pivot pin 6 to guide pin 4 in guide slot 5.

It will be appreciated that the illustrated positions of certain components of the various elements may be reversed, if desired. That is, elements that have been disclosed hereabove as being carried by portion 1, e.g., pivot pin 6, guide pin 4, etc., could instead be carried by portion 2, and vice versa. For purposes of simplicity or discussion, however, such alternative embodiments will not be addressed in detail, it being understood that their structural details and operation fall within the metes and bounds of the present invention. Therefore, while presently preferred embodiments of practicing the invention have been shown and described with particularity in connection with the accompanying drawings, the invention may be otherwise embodied within the scope of the following claims.

What is claimed is:

1. A hinged clamp mechanism for holding a body part during a monitoring procedure, the mechanism comprising:
   a first portion;
   a second portion;
   a guide pin attached to one of the first and second portions and movable along a guide slot provided in the other of the first and second portions;
   a separable pivotal connection between the first portion and the second portion for enabling opening of a space therebetween so as to permit the insertion of the body part between the first and second portions;
   yieldable biasing means, connected at one end to the guide pin and at the other end to the other of the first and second portions that is provided with the guide slot, for causing the guide pin to act as a pivot point and for causing the first and second portions to apply uniform pressure along a desired length of the body part upon insertion of the body part between the first and second portions; and
   wherein the separable pivotal connection is located between the ends of the yieldable biasing means.

2. A hinged clamp mechanism for holding a body part during a monitoring procedure as described in claim 1 wherein the separable pivotal connection for enabling opening of a space between the first portion and the second portion comprises a pivot pin carried by an inner surface of one of the first and second portions separably engaging a corresponding pivot seat carried by an inner surface of the other of the first and second portions.

3. A hinged clamp mechanism for holding a body part during a monitoring procedure as described in claim 1 wherein the separable pivotal connection for enabling opening of a space between the first portion and the second portion comprises two pivot pins connected to one of the first and second portions and two corresponding pivot seats connected to the other of the first and second portions, such that a set including a pivot pin and a corresponding pivot seat is located on each side of the hinged clamp mechanism.

4. A hinged clamp mechanism for holding a body part during a monitoring procedure as described in claim 1 wherein the guide pin and guide slot comprise a fixed guide pin carried by one of the first and second portions and inserted into a guide slot provided in the other of the first and second portions such that the guide pin connects the first portion to the second portion and is movable within the guide slot.

5. A hinged clamp mechanism for holding a body part during a monitoring procedure as described in claim 4 wherein two guide pins and two corresponding guide slots are used and form two pairs of connectors, one of each pair being located on each side of the hinged clamp mechanism such that a body part can be inserted therebetween.

6. A hinged clamp mechanism for holding a body part during a monitoring procedure as described in claim 1 wherein the yieldable biasing means comprises a leaf spring.

7. A hinged clamp mechanism for holding a body part during a monitoring procedure as described in claim 6 wherein two leaf springs are used, one on each side of the clamp mechanism.

8. A hinged clamp mechanism for holding a body part during a monitoring procedure as described in claim 1 wherein the yieldable biasing means comprises a coiled wire torsion spring.

9. A hinged clamp mechanism for holding a body part during a monitoring procedure as described in claim 8 wherein two coiled wire torsion springs are used, one on each side the clamp mechanism.

10. A hinged clamp mechanism for holding a body part during a monitoring procedure as described in claim 1 wherein at least one of the first and second portions further comprise a preformed surface for conforming to and holding the body part.

11. A hinged clamp mechanism for holding a body part during a monitoring procedure as described in claim 1 wherein at least one of the first and second portions further comprise a pliable material on the inner surface thereof that will conform to the body part being held.

12. A sensor for holding and testing a body part comprising:
    an upper portion;
    a lower portion;
    a movable guide pin and slot connecting the upper portion to the lower portion;
    a separable pivotal connection between the upper portion and the lower portion for enabling opening of a space therebetween so as to permit the insertion of the body part between the upper and lower portions,
    a yieldable biasing element connected to the upper portion and the lower portion for causing the movable guide pin to act as a pivot point and for causing the upper and lower portions to apply uniform pressure along a desired length of the body part upon insertion of the body part between the upper and lower portions;
    a signal emitting means positioned in the upper portion; and
    a signal receiving means positioned in the lower portion such that a signal from the signal emitting means passes through the body part and into the signal receiving means.

13. A sensor as described in claim 12 wherein the separable pivotal connection for enabling opening of a space between the upper portion and the lower portion comprises a pivot pin protruding from an inner surface of the upper portion separably engaging a corresponding pivot seat protruding from an inner surface of the lower portion.

14. A sensor as described in claim 12 wherein the separable pivotal connection for enabling opening of a space between the upper portion and the lower portion comprises two pivot pins connected to the upper portion and two corresponding pivot seats connected to the lower section, such that a set including a pivot pin and a corresponding pivot seat is located on each side of the sensor.

15. A sensor as described in claim 12 wherein the guide pin and guide slot comprise a fixed guide pin protruding from the upper portion and inserted into a guide slot fixed in the lower portion such that the guide pin connects the upper portion to the lower portion and is movable within the guide slot.

16. A sensor as described in claim 15 wherein two guide pins and two corresponding guide slots are used and form two pairs of connectors, one of each pair being located on each side of the sensor such that a body part can be inserted therebetween.

17. A sensor as described in claim 12 wherein the yieldable biasing element comprises a leaf spring.

18. A sensor as described in claim 17 wherein two leaf springs are used, one on each side of the sensor.

19. A sensor as described in claim 18 wherein each leaf spring is connected at one end to the guide pin and at the other end to the lower portion containing the guide slot and wherein the separable pivotal connection is located between the ends of the leaf springs.

20. A sensor as described in claim 12 wherein the yieldable biasing element comprises a coiled wire torsion spring.

21. A sensor as described in claim 20 wherein two coiled wire torsion springs are used, one on each side of the sensor.

22. A sensor as described in claim 12 wherein at least one of the upper portion and the lower portion further comprise a preformed surface for conforming to and holding the body part.

23. A sensor as described in claim 12 wherein at least one of the upper portion and the lower portion further comprise a pliable material on the inner surface thereof that will conform to the body part being held.

* * * * *